United States Patent
Kassab et al.

(10) Patent No.: US 8,398,703 B2
(45) Date of Patent: Mar. 19, 2013

(54) DEVICES AND METHODS FOR MAGNETIC TISSUE SUPPORT

(75) Inventors: Ghassan S. Kassab, Zionsville, IN (US); Jose A. Navia, Sr., Buenos Aires (AR)

(73) Assignee: CVDevices, LLC, Zionsville, IN (US)

( * ) Notice: Subject to any disclaimer, the term of this patent is extended or adjusted under 35 U.S.C. 154(b) by 572 days.

(21) Appl. No.: 11/997,147

(22) PCT Filed: Jul. 28, 2006

(86) PCT No.: PCT/US2006/029424
§ 371 (c)(1),
(2), (4) Date: Jun. 30, 2008

(87) PCT Pub. No.: WO2007/016348
PCT Pub. Date: Feb. 8, 2007

(65) Prior Publication Data
US 2008/0300672 A1 Dec. 4, 2008

Related U.S. Application Data

(60) Provisional application No. 60/703,421, filed on Jul. 29, 2005.

(51) Int. Cl.
*A61F 2/06* (2006.01)
(52) U.S. Cl. ..................................................... 623/1.15
(58) Field of Classification Search .................. 606/108, 606/151, 153–156, 194, 200; 623/1.11, 1.15, 623/1.23
See application file for complete search history.

(56) References Cited

U.S. PATENT DOCUMENTS

| | | | |
|---|---|---|---|
| 4,531,933 A * | 7/1985 | Norton et al. | 604/8 |
| 6,673,104 B2 | 1/2004 | Barry | |
| 6,719,768 B1 | 4/2004 | Cole et al. | |
| 2004/0088008 A1* | 5/2004 | Gannoe et al. | 607/1 |
| 2005/0090843 A1 | 4/2005 | Bolduc | |
| 2006/0041281 A1* | 2/2006 | Von Arx et al. | 607/18 |
| 2006/0264982 A1* | 11/2006 | Viola et al. | 606/153 |

OTHER PUBLICATIONS

International Searching Authority, International Search Report, Apr. 3, 2007.
International Searching Authority, Written Opinion of the International Searching Authority, Apr. 3, 2007.
Lu et al., "The Effect of Magnetic Stent on Coronary Restenosis After Percutaneous Transiuminal Coronary Angioplasty," Chinese Medical Journal, Aug. 2001, 114 (8), p. 821-23.

* cited by examiner

*Primary Examiner* — Ryan Severson
*Assistant Examiner* — Ashley Cronin
(74) *Attorney, Agent, or Firm* — Reichel IP LLP; Mark C. Reichel; Kevin R. Erdman

(57) ABSTRACT

Devices and methods are disclosed for providing tissue support within the body. A metallic component and a magnetic component are used and allowed to interact through the body of the tissue such that the attractive forces between these components provides the external support needed by that tissue to properly function within its position. Such a technique is described with respect to the particular example of correction of aneurysms.

22 Claims, 3 Drawing Sheets

DEVICES AND METHODS FOR MAGNETIC TISSUE SUPPORT

RELATED APPLICATIONS

The present application is a U.S. National Stage Application of the International Patent Application Serial No. PCT/US2006/29424, filed Jul. 28, 2006, which claims priority to U.S. Provisional Patent Application Ser. No. 60/703,421, filed Jul. 29, 2005. The contents of both of these applications are hereby incorporated by reference in their entirety into this disclosure.

BACKGROUND OF THE INVENTION

1. Field of the Invention

The present invention relates generally to tissue support. More particularly, the present invention relates to devices and methods for magnetic aortic tissue support.

2. Background of the Invention

Aortic aneurysms are formed in a vessel when the wall of the vessel weakens, either due to disease, aging, heredity or some other process. The pressure of the blood flowing through the weakened area causes the vessel wall to balloon out, forming a blood-filled aneurysm sack. Although most aneurysms begin small, they tend to enlarge over time and the risk of the sack rupturing increases as the aneurysms grow larger. Acute rupture of the aortic aneurysm is a life-threatening event, due to massive internal bleeding with a mortality rate of 75-80%. According to the Society of Vascular Surgeons, ruptured aneurysms account for more than 15,000 deaths in the U.S. each year, making the abdominal aortic aneurysm (AAA) the 13.sup.th leading cause of death in the USA. Clearly, early detection and rupture prevention is the key to the final outcome in abdominal aortic aneurysm patient. However, the condition is under-diagnosed because most patients with AAA are asymptomatic. Consequently, the majority of the anomalies are discovered unexpectedly during routine tests or procedures. An estimated 1.7 million Americans have AAA, but only about 250,000-300,000 patients are diagnosed every year.

There is no proven medical treatment, and surgical repair has been the only common therapeutic option. A standard open repair has been associated with significant morbidity and mortality, prolonged recovery, and late complications. Because of these limitations, many patients and their physicians choose to defer operative treatment. Recently, endovascular aneurysm repair (EVAR) has become an alternative and some studies favorably compare endovascular repair with a standard open repair. However, significant concern exists relating to endovascular repair and its value is a subject of healthy debate. Endovascular abdominal aortic aneurysm repair has gained acceptance as a minimally invasive alternative to open surgery in selected patients. While long-term durability remains uncertain, patients and their physicians are willing to accept a degree of uncertainty in exchange for dramatic reduction in duration of hospital stay, and need for blood transfusion. Hence, improvements in the current EVAR devices can potentially make this approach standard for AAA repair.

Most patients diagnosed with AAA are not considered for surgery or endovascular repair unless the aneurysm is at least 5 cm in diameter, the point at which the risk of rupture clearly exceeds the risk of repair. Those with a smaller aneurysm are followed closely with regular imaging studies. There has been much speculation over the years about the preventive use of endovascular aneurysm repair in patients with aneurysms smaller than 5 cm, however, vascular surgeons so far have been reluctant to use EVAR for smaller aneurysms due to the concern about the long term durability of the technology and the lack of data demonstrating a clear benefit of early intervention. Moreover, although EVAR outcomes have improved over the years as physicians gain more experience with the procedure, it remains a technically demanding procedure that requires extensive training and this has limited the number of physicians qualified to perform EVAR.

Despite the shortcoming relating to training, a number of endovascular devices have been evaluated in clinical trials designed to gain approval from governmental agencies. These devices differ with respect to design features, including modularity, metallic composition and the structure of the stent, thickness, porosity, chemical composition of the polymeric fabric, methods for attaching the fabric to the stent, and presence or absence of an active method of fixing the device to the aortic wall with bars or hooks. With consideration of the numbers of structural variations between different brands of endovascular devices, it would be remarkable if clinical outcome were not equally dissimilar. Parameters such as frequency of endoleak, long-term change in size of the aneurysm sack, reason for device migration and limb thrombosis may be linked to specific device design features. Hence, any improvements in the deployment and attachment of stent graft would increase the utility of EVAR.

Important drivers and limiters of EVAR are playing a big role in the decision of the treatment. The drivers include: 1) Less invasive compared to open repair, which translates into shorter hospitalization and recovery and lower major morbidity; 2) Aging of the population will increase the incidence and prevalence of AAA and thoracic aortic aneurysm (TAA); 3) Increasingly informed patient population will generate strong patient demand for minimally invasive therapy, and 4) Next-generation devices, expected to address wider patient population (including those with thoracic disease) and reduce complications relative to current model. The limiters, on the other hand, include the following: 1) Clinical literature does not support prophylactic endovascular treatment of the small aneurysm with a low risk of fracture; 2) High rate of late complication necessitates extensive and potentially life-long post procedural follow-up (not required for open repair) and repeat intervention that makes endovascular therapy potentially more costly than open surgery; 3) Current device is not applicable to full-range of AMA patients; 4) Technical demands of the approach require devices and time-consuming training that may eliminate rapid adoption of new products, particularly for a specialist with a smaller case load, and 5) Surgical conversion is complicated by the presence of the stent graft. Improvements in the current devices would certainly make the drivers outweigh the limiters.

The most important trial conducted to date is the EVAR 1 study, which randomized over 1,000 elective patients with aneurysms 5.5 cm or larger comparing EVAR to open surgical repair. Thirty-day mortality published this year demonstrated a clear advantage of EVAR (1.6% vs. 4.7% for open repair). However, EVAR patients had significantly higher rates of secondary intervention (9.8% vs. 5.8%). A second version study, EVAR 2, is comparing EVAR with best medical treatment in patients unsuitable for surgical repair. The 12-month result for EVAR 1 are particularly important, as physicians will be looking to see if endovascular therapy is able, for the first time, to demonstrate significant survival benefit over open surgery after one year.

Despite some of its inherent drawbacks, EVAR is expected to experience robust growth over the next several years. The U.S. AAA graft market is projected to increase from $288 M in 2004 to $552 M in 2008. In addition, contribution from thoracic graft systems, beginning this year, will grow the total US aortic stent market to over $670M in 2008 (Endovascular, 2005).

Ongoing areas of concern with endovascular abdominal aortic repair are; 1) Rate of late complications; 2) Appreciable intervention and conversion rates; 3) Dubious cost advantage compared to open surgery due to the need of intervention and regular patient monitoring; 4) Increased device failure with time; 5) Increased procedural failure with time, and 6) Rupture risk of 1% per year after endovascular repair is not dramatically different from the natural history of small 5 cm aneurysms. Hence, there is high rate of secondary intervention (primarily to treat endoleaks—persistent flow within the aneurysm sack that in certain cases can lead to aneurysm rupture, if left untreated), and increasing rate of device failures over time. In addition to endoleaks, other late complications in AAA graft trials include device migration, modular component separation, graft thrombosis, bar separation, and material fatigue.

Currently in the U.S., about 60,000 abdominal aortic aneurysm (AAA) patients require intervention each year. The majority of the patients are treated with open surgical repair, while about 40% are treated with EVAR. Although open AAA repair is highly successful, it is also extremely invasive, with an operative mortality rate between 5-10%. Thus, patients with significant co-morbidities are generally not candidates for open repair. These patients are the primary beneficiaries of endovascular grafting or EVAR. EVAR gained tremendous popularity in 1990 after commercial AAA stent graft became available in the U.S. After a one-year period of adjustment, however, problems with the first generation device began to surface including migration, endoleak and endotension. Although physicians remain confident, they have for the most part recovered from the disappointment associated with the first generation technology and are looking forward to future advances in the field. Further expansion of endovascular repair is required to improve the device and good long-term results from large randomized trials comparing EVAR with open surgery. There is no doubt that a device that overcomes some of the current shortcomings of EVAR devices such as migration, endoleak and endotension is greatly welcomed for the treatment of aortic aneurysm.

Thus, a need exists in the art for an alternative to the conventional methods of aneurysm treatment. A further need exist for a reliable, accurate and minimally invasive device or technique of treating aneurysms and minimizing their risks of enlarging or rupturing.

SUMMARY OF THE INVENTION

The current EVAR devices and methods are inadequate. They are prone to such fatal problems as migration, endoleak, and endotension. In order to address this medical problem, the present invention provides devices and methods for minimizing and/or preventing the growth or rupture of aneurysms or other vascular growth through the use of magnetic tissue support.

In one exemplary embodiment, the present invention is a magnetic device for controlling the growth of an aneurysm. The device includes a metallic body positioned within a lumen of an aneurysm, wherein an end-to-end length of the metallic body extends at least along a longitudinal length of the aneurysm; and a magnet in communication with the metallic body to hold the body in position within the lumen of the aneurysm.

In another exemplary embodiment, the present invention is a magnetic device for controlling the growth of an aneurysm. The device includes a metallic body positioned within the lumen of an aneurysm, wherein an end-tend length of the metallic body extends at least along a longitudinal length of the aneurysm; and a tube with openings located on an outer surface of the metallic body, wherein the tube with openings is used to control the fluid environment in the area between the outer surface of the metallic body and an inner wall surface of the aneurysm; and a magnet in communication with the metallic body to hold the body in position within the lumen of the aneurysm.

In yet another exemplary embodiment, the present invention is a method for magnetic tissue support. The method includes introducing a metallic body on one side of a tissue that needs support; and introducing a magnet on the opposite side of the tissue that needs support so that the magnet and the metallic body form an attractive force across the body of the tissue that needs support, thereby providing support to the tissue.

As discussed above, conventional endovascular aneurysm repair (EVAR) is done through the use of stent grafts introduced into the aorta percutaneously. Some major problems with the current approach include migration, endoleak and endotension, all of which ultimately lead to aneurysm rupture or acute vessel thrombosis or occlusion. The present invention provides a device that relates to the use of a ferromagnetic stent graft (internal of vessel) and a magnet ring (external to vessel) to provide mechanical support for aortic aneurysm. The use of magnetic attachment (proximal and distal on the graft) with sufficient adhesion force is intended to eliminate device migration. The compressive adhesive magnetic force at the two ends of the aneurysm is designed to prevent endoleak and endotension. As used herein and throughout the application, "proximal" is used to refer to a region closer to the heart (e.g. superior) when the human body is viewed from the anatomical position and "distal" is used to refer to a region farther from the heart (e.g., inferior) when the human body is viewed from the anatomical position.

Some of the considerations in the present invention include: (1) designing the geometry and magnetic properties of the two poles of the magnet (stent and magnetic ring) to produce the necessary Maxwell force acting on the aortic tissue that prevents migration, endoleak and endotension; and (2) validating the design obtained in an in vitro system using porcine aorta with an aneurysm.

As presented herein, the ferromagnetic stent graft and magnet system provide sufficient mechanical adhesive force to prevent migration, endoleak and endotension. A strategy is to optimize the design of the geometry and material magnetic properties to produce stresses on the level of those experienced by the aorta under physiological conditions.

DETAILED DESCRIPTION OF THE INVENTION

Figure 1:
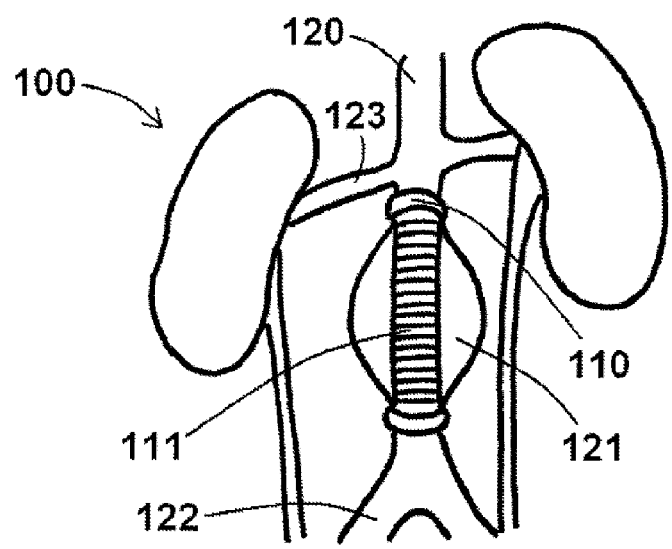
FIG. 1 shows a front view of a magnetically stabilized luminal stent graft assembly with two magnetic bodies according to an exemplary embodiment of the present invention.

To better understand the advantages of the present invention over any of the techniques currently available in the conventional arts, it is useful to consider the science behind the motivation for the present invention.

As discussed briefly above, the aneurysm size appears to be the one of the most important factors determining risk of aneurysm rupture. Changes in aneurysm dimension have been used as a surrogate marker for clinical efficacy after endovascular repair. Other morphological changes, including progressive angulation, and aortic neck enlargement, may occur in response to either aneurysm exclusion or associated degenerative changes in adjacent segments, respectively. In endovascular repair, the aneurysm sack is left intact and, as a consequence, this feature plays an important role in outcome assessment, defining the success or failure of aneurysm exclusion. Long term aneurysm exclusion and device stabilization is dependent on the maintenance of an effective attachment, connection, or seal between the endograft and the host aorta. Therefore dilatation of the aorta at the site or sites intended for primary endograft fixation may lead to treatment failure either with device migration or via the occurrence of a new endoleak with aneurysm expansion. The use of magnets as described in the present invention is intended to reduce the neck enlargement and remodeling since the magnet will distribute the stress more uniformly unlike the stent that pose stress concentration which induce vascular remodeling.

Endoleak is defined by the persistence of blood flow outside the lumen of the endoluminal graft but within the aneurysm sack, as determined by an imaging study. An endoleak is evidence of incomplete exclusion of the aneurysm from the circulation and may be the result of an incomplete seal between the endograft and the blood vessel wall, an inadequate connection between components of a modular prosthesis, fabric defects or porosity, or retrograde blood flow from patent aortic side branches. Hence, an adhesive force at the neck of the stent may minimize or prevent endoleak (type I).

Endoleaks, including their detection, potential clinical significance, and treatment remain an active area of investigation. However, although it is now evident that an endoleak may resolve spontaneously, a proportion of those that do persist have been associated with late aneurysm rupture. Endoleaks classification include:

| 1. | Type I: | a) Inadequate seal at the proximal end of endograft<br>b) Inadequate seal at the distal end of endograft<br>c) Inadequate seal at the iliac occluder plug |
|---|---|---|
| 2. | Type II: | Flow from visceral vessels (lumbar, IMA, accessory renal, Hypogastric) without attachment site connection. |
| 3. | Type III: | a) Flow from module disconnection<br>b) Flow from fabric disruption (Minor < 2 mm, Major > 2 mm) |
| 4. | Type IV: | Flow from porous fabric (<30 days after graft placement) |

There are also endoleaks of undefined origins where flow is visualized but the source is unidentified.

Endotension—It is now appreciated as AAA may continue to enlarge after endovascular repair, even in the absence of detectable endoleak, and that this enlargement may lead to aneurysm rupture. Explanation for persistence or recurrent pressurization of an aneurysm sack includes blood flow that is below the sensitivity limits for detection with current imaging technology, or pressure transmission through thrombus, or endograft fabric. On physical examination, the aneurysm may be pulsatile and intrasac measurements may reveal pressure that approach or equal to systemic values. A magnetic device according to the present invention that provides sufficient "seal" at the two necks of the aneurysm and along the body of the aneurysm would eliminate endoleaks type I and II.

Migration—Migration is defined by clinical and radiographic parameters, as a caudal movement of the proximal attachment site or cranial movement of a distal attachment site. A device is considered to have migrated if at least 10 mm of movement was noted relative to anatomic landmarks, a patient experiences a symptom from migration, irrespective of distance, or a secondary intervention was undertaken to remedy migration-related problems, irrespective of distance. An adhesive force with sufficient shear component would also eliminate migration. Hence, one of the advantages of the present invention is the development of a magnet-based anchoring device at the two ends of the graft that overcomes endoleak and migration.

In biomedical engineering, the electromagnetic effect on biological cells has diverse applications such as MRI, bypass surgery, and MEMS-related devices. Static and time-dependent fields are used in the diagnosis and treatment of human disease. MRI involves using a large magnetic field to image structure. The therapeutic benefits of low frequency magnetic fields have been shown to induce gene expression and upregulate the heat shock protein. Recently, magnets are advocated for use in vascular coupling for distal anastomosis in bypass surgery, which has lead to a multi-center clinical trial. To date, most of the magneto-static research on biological cells is investigated by using analytic or numerical finite difference methods.

The fundamental equations governing the interaction between current and magnetic-flux density can be found in any classic textbook. In general, those equations are complex due to the fact that matter possesses a great variety of properties. For example, if the body of interest is elastic, then a change of shape, volume and temperature can appear. Also, if the sum of all forces acting on the body is not zero, translational or rotational acceleration may occur. Therefore, it is important to calculate the Magnetostatic forces and couple the Magnetostatic forces with other physical effects in order to determine the deformation, rotation, displacement and so on in the matter. In the present application, the force balance including the Maxwell's force is analyzed and simulated based on the distribution of the magnetic-flux density. The coupled formulation of the magnetic field and the surface stress balance for treatment of aortic aneurysm is demonstrated.

In general the magnetic field intensity is not curl-free and, therefore, we cannot describe R in terms of a scalar function. However, there are a number of important applications in magnetics in which a magnetic field exists, but there are no current densities involved. The most obvious are those involving permanent magnets. Here we consider a concentric annulus of the stent graft internal to the vessel lumen and the permanent magnetic ring external to the vessel wall as shown in FIG. 1. Since the magnetic ring does not cover the entire circumference of the vessel (covers 0 to 270°), the solution must be numerical. To design the geometry and magnetic properties of the two poles of the magnet (stent and magnetic ring) to produce the necessary Maxwell force acting on the aortic tissue that prevents migration, and endoleak.

A three-dimensional Laplace's equation describes the solution for the potential field in cylindrical coordinates ($\rho,\phi,z$):

$$\frac{\partial^2 \Phi}{\partial \rho^2} + \frac{1}{\rho}\frac{\partial \Phi}{\partial \rho} + \frac{1}{\rho^2}\frac{\partial^2 \Phi}{\partial \phi^2} + \frac{\partial^2 \Phi}{\partial z^2} = 0 \quad (1)$$

The separation of variables Is accomplished by the substitution:

$$\Phi(\rho,\phi,z) = R(\rho)Q(\phi)Z(z) \quad (2)$$

This leads to three ordinary differential equations:

$$\frac{d^2 Z}{dz^2} - k^2 Z = 0 \quad (3a)$$

$$\frac{d^2 Q}{d\phi^2} + v^2 Q = 0 \quad (3b)$$

$$\frac{d^2 R}{d\rho^2} + \frac{1}{\rho}\frac{dR}{d\rho} + \left(k^2 - \frac{v^2}{\rho^2}\right)R = 0 \quad (3c)$$

The solutions of the first two equations are elementary:

$$Z(z) = e^{\pm kz} \quad (4a)$$

$$Q(\phi) = e^{\pm v\phi} \quad (4b)$$

The radial equation can be put in a standard form by the change of variable $x=k\rho$. Then it becomes $$\frac{d^2 R}{dx^2} + \frac{1}{x}\frac{dR}{dx} + \left(1 - \frac{v^2}{x^2}\right)R = 0 \quad (5)$$

This is Bessel's equation, and the solutions are called Bessel functions of order $v$. When $v=m$ is an integer and k is a constant to be determined. The radial factor is $$R(\rho) = CJ_m(k\rho) + DN_m(k\rho) \quad (6)$$

Finally, we get $$\Phi(\rho,\phi,z) = (Ae^{\pm kz})(Be^{\pm v\phi})[CJ_m(k\rho) + DN_m(k\rho)] \quad (7)$$

where A, B, and C are the unknown constant. If we combine equation (7) and boundary conditions, we can solve any type of magnetic field between the partial (0° to 270°) concentric annulus.

When the distribution of the magnetic field is known, the Maxwell's stress tensor can be calculated by the following formulation after the coordinate system transformation from the cylindrical coordinate to the rectangular coordinate.

$$T_{ij} = \frac{1}{\mu}\left[B_i B_j - \frac{1}{2}B^2 \delta_{ij}\right] \quad (8)$$

(Maxwell's Stress Tensor)

where
$T_{ij}$: Maxwell's stress tensor [N/M², Newton/square meter]; $\delta_{ij}$: Kronecker delta; $B_i$: magnetic-flux density T, Tesla or Wb/m², weber/meter²]; $H_i = \mu B_i$; magnetic field intensity [N/(A·m), weber/(ampere·meter)]; $\delta_{ij}$≡1 if i=j; $\delta_{ij}$≡0 if i≠j.

In Matrix form, $$T_{ij} = \begin{bmatrix} \mu H_x^2 - \frac{1}{2}\mu|H|^2 & \mu H_x H_y & \mu H_x H_z \\ \mu H_x H_y & \mu H_y^2 - \frac{1}{2}\mu|H|^2 & \mu H_y H_z \\ \mu H_x H_z & \mu H_y H_z & \mu H_z^2 - \frac{1}{2}\mu|H|^2 \end{bmatrix} \quad (9)$$

(Maxwell's Stress Tensor)

Once the Maxwell's stress tensor is computed, the equilibrium force balance in the surface layer of the artery may be presented.

$$\sigma_{ji,j} + T_{ji,j} + f_j = 0 \text{(Equilibrium equation for static case)} \quad (10)$$

where $\sigma_{ji}$ is the stress tensor [N/M², Newton/square meter] and $f_i$ is the force [N/M³, Newton/cubic meter].

Once the Maxwell stress is computed, we must calculate the Maxwell force. Elementary theory relates magnetostatic forces to changes in the total magnetic field energy when infinitesimal virtual displacements are made between magnetic elements.

$$F = \frac{\partial}{\partial R}\int \frac{B \cdot H}{2} dv \quad (11)$$

An alternative method using the Maxwell Stress Tensor allows magnetostatic forces to be calculated directly without approximating the limit of a virtual displacement. Instead, integration of the stress tensor $T_{ij}$ over any surface enclosing the object will give the net force acting on it directly if we assume that the permeability of the surrounding tissue (vessel wall and blood) is significantly different than that of the permanent magnets. If n is the outward normal to the surface, the Maxwell force may be computed as follows:

$$F = \int T_{ij} \cdot n \, ds \quad (12)$$

Expanding the dot product $T_{ij}$·n allows the force integral equation (19) to be written explicitly as $$F = \frac{1}{\mu_0}\oint \left[(B \cdot n)B - \frac{1}{2}B^2 n\right] ds = \mu_0 \oint \left[(H \cdot n)H - \frac{1}{2}H^2 n\right] ds \quad (13)$$

The stress vector $$P = \mu_0\left[(H \cdot n)H - \frac{1}{2}H^2 n\right]$$

does not generally point along H. However for the two extreme cases of the H field either normal or parallel to the surface, the forces are either attractive or repulsive across the surface. But when the field crosses the surface at any other angle than 0° or 90°, there will be a shear component to the force which acts in the plane of the surface When 3-D axis migration occurs, the magnetic fields H will change so that the axis force will be created in order to prevent the migration. This requires numerical method such as the FEM simulation.

An exemplary embodiment of the present invention as used in graft assembly 100 is shown in FIG. 1. Assembly 100 includes magnetic bodies 110 and magnetic polymer graft 111. In this embodiment, the magnetic bodies 110 may be situated at the proximal and distal ends of magnetic polymer graft 111 which may be positioned distal to the renal arteries 123 and proximal to the common iliac arteries 122 as shown in FIG. 1. The magnetic bodies 110 may cover part or the entire circumference of the abdominal aorta 120. The magnetic bodies 110 are shown to be ring-shaped in FIG. 1, but they can be any other shape (e.g., staple-shaped, etc.) as long as they are able to provide a sufficient magnetic attractive force on the magnetic polymer graft 111 to stabilize the magnetic polymer graft 111 on the inner surface of the aorta 120.

The magnetic polymer graft 111 may be situated inside the abdominal aorta 120 or the aneurysmic sack 121 and the magnetic bodies 110 may be situated external to the wall of the abdominal aorta 120 or the aneurysmic sack 121 as shown in FIG. 1. The magnetic bodies 110 may be composed of a material such that they produce a high magnetic field with a low mass and should be stable against demagnetization. When a ferromagnetic material is magnetized in one direction, it will not relax back to zero magnetization when the imposed magnetizing field is removed. The amount of magnetization it retains at zero driving field is defined as remanence. The amount of reverse driving field required to demagnetize it is called coercivity. Some compositions of ferromagnetic material will retain an imposed magnetization indefinitely and are useful as permanent magnets. NdFeB (Neodymium Iron Boron) is an example of a permanent magnet used in biological applications including sutureless vascular anastomosis with magnets.

The magnetic bodies 110 may stabilize the magnetic polymer graft 111 at the proximal and distal ends of the magnetic polymer graft 111 thereby preventing movement of the magnetic polymer graft 111 or endoleak or endotension. The magnetic polymer graft 111 may be uniformly composed of a metallic material commonly used in the medical arts such that the magnetic bodies 110 may exert an attractive force on the metallic material such that the magnetic polymer graft 111 is held in position by the magnetic bodies 110 on the proximal and distal ends of the magnetic polymer graft 1l as illustrated in FIG. 1. Alternatively, the magnetic polymer graft 111 may be composed of metallic material only at its proximal and distal ends such that the magnetic bodies 110 may be properly positioned to exert an attractive force on these proximal and distal ends of magnetic polymer graft 111. In this variation, the body of the magnetic polymer graft 111 may be mesh-like and may be composed of any material commonly used in the medical stenting arts (e.g., polytetrafluorethylene—PTFE) such that it can house the metallic material at its proximal and distal ends. The magnetic polymer graft 111 may act as a stent by providing a structural passageway for blood to flow down the abdominal aorta 120 while avoiding contact with the aneurysmic sack 121.

A number of different delivery methods may be used to introduce the magnetic bodies 110 in place. Such methods are also applicable to the other exemplary embodiments presented below. Various delivery methods include, but are not limited to: (a) an abdominal laparoscopic procedure (AAA) or thoracoscopic procedure (TAA); (b) a minimal surgical procedure; or (c) an open surgical procedure. Other methods and procedures are apparent to one having ordinary skill in the art after consideration of the present exemplary embodiments and are, thus, within the scope of the present invention.

Figure 2:
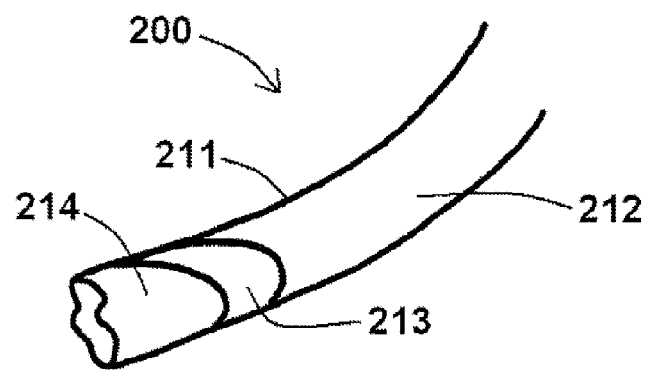
FIG. 2 shows an angled view of a luminal stent graft with a magnetic covering and powder according to an exemplary embodiment of the present invention.

Another exemplary embodiment of the present invention is presented as assembly 200 and is shown in FIG. 2. Assembly 200 depicts a magnetic polymer graft 211 which includes a magnet cover 212, bonded magnet powder 213, and a graft lumen 214. The bonded magnet powder 213 of the magnetic polymer graft 211 may be composed of any material commonly used in the medical magnetic arts. The graft lumen 214 may be formed using materials commonly used in the medical stent arts (e.g., polytetrafluoroethylene—PTFE). The graft lumen 214 may allow blood to pass through its material and thereby prevent contact with the aneurysm (not shown) and it may be of such a diameter as to achieve the optimal or desired volume of blood flow through the aneurysm.

The magnetic polymer graft 211 may interact with magnetic bodies (not shown) situated on the external wall of the abdominal aorta or aortic aneurysm (not shown). In this way, the magnetic polymer graft 211 can be held in place by the attractive force being exerted on it by the magnetic bodies (not shown). Thus, the bonded magnet powder 213 can be situated inside a magnet cover 212 which may be the external layer of the magnetic polymer graft 211. The magnet cover 212 may act to protect and confine the magnet powder 213 and further serve to make contact with the inside of the abdominal aorta or aortic aneurysm. This configuration would provide the bonded magnetic powder 213 maximum communication with the magnetic bodies (not shown) situated on the external wall of the abdominal aorta or aortic aneurysm. The magnetic polymer graft 211 may be inserted through endovascular procedure into the patient thereby avoiding the complications associated with other invasive techniques.

Figure 3A:
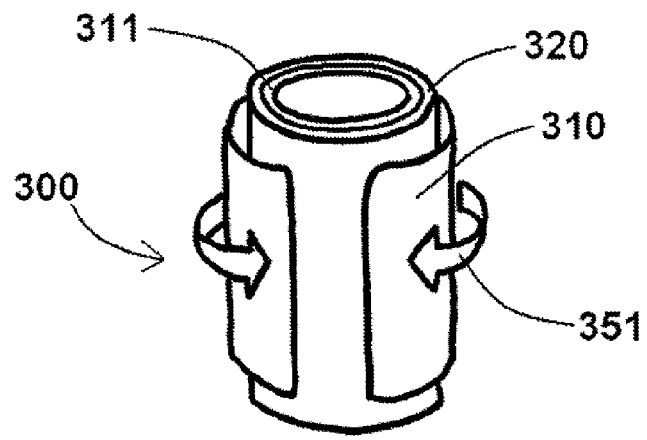
FIG. 3A shows a front view of a luminal stent graft embedded with magnetic beads or particles surrounded by a stabilizing magnetic body to prevent distension of the aneurysmic region according to an exemplary embodiment of the present invention.

Yet another exemplary embodiment of the present invention as shown in graft assembly 300 is presented in FIG. 3A. Assembly 300 includes magnetic body 310 and magnetic polymer graft 311. The magnetic body 310 is depicted as being ring-shaped in FIG. 3A but it may be any other shape as described above. The magnetic body 310 may cover part or the entire circumferential surface of the abdominal aorta 320. In the latter case, the magnetic body 310 may partially ensheathe the abdominal aorta 320 such that the magnetic body 310 is provided with enough surface area to interact with the magnetic polymer graft 311 on the inside of the abdominal aorta 320 thereby allowing a sufficient magnetic force to be applied to the magnetic polymer graft 311. The directional arrows 351 illustrate the manner in which the magnetic body 310 may ensheathe the abdominal aorta 320 (e.g., circumferentially) to allow for optimal interaction between the magnetic body 310 and the magnetic polymer graft 311.

Figure 3B:
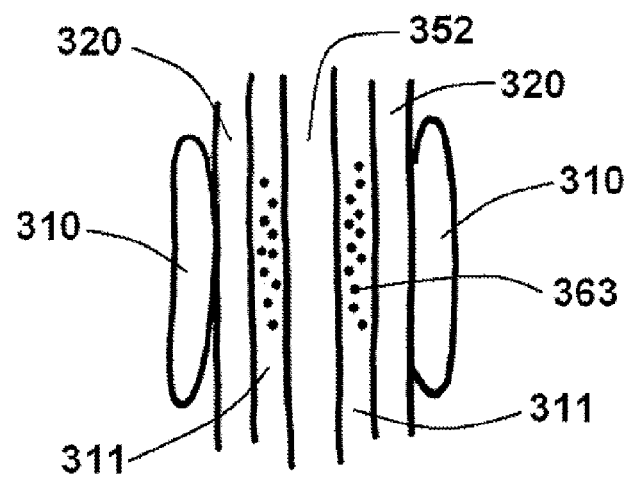
FIG. 3B shows a cross-section of FIG. 3A to emphasize axial support of the diseased region.

FIG. 3B shows a cross-section of assembly 300. The lumen 352 of the graft 311 may provide a conduit for the blood to flow through the aneurysmic sack (not shown) such that the blood flow does not contact the aneurysmic sack (not shown). The outer surface of the abdominal aorta 320 may be in physical contact with the magnetic body 310 as illustrated in FIG. 3B. The magnetic polymer graft 311 may make physical contact with the inner surface of the abdominal aorta 320 such that the magnetic polymer graft 311 is fitted tightly enough against the inner surface of the abdominal aorta 320 in order to prevent blood leakage out of the graft 311 and into the aneurysmic sack (not shown) via space between the proximal portion of the graft 311 and the inner surface of the abdominal aorta 320. This particular embodiment may also prevent endoleak type II and may further incorporate magnetic beads or particles 353 along the body of graft composite as shown in FIG. 3B. Application of magnetic body 310 external to the abdominal aorta 320 in the form of gel or glue on the adventitial surface may also provide a restrictive force which will prevent expansion of aorta against endoleak type II or endotension.

In this embodiment, we may consider the magnetic flux density B, which plays the significant role in the computation of attraction forces. The magnetic polymer graft 311 may include, for examples polymer-bonded Nd—Fe—B magnets (BNP-8) by compression moulding (polymer-bonding: magnet powders are mixed with a polymer carrier matrix, such as epoxy). The magnetic bodies 310 are formed in a certain shape, when the carrier is solidified, which has residual induction Br (0.6-0.65 Teslas or 6000-6500 Gauss); the ring consists of, for example, Heusler alloy ($Fe_{80}B_{20}$), which has the saturation magnetic flux density of 0.1257 Teslas (=1257 Gauss); or consists of carbon-coated metal particles, which has saturation magnetization exceeding about 120 emu/g (saturation magnetic flux density≅0.15 Teslas). The properties provide sufficient force to support the abdominal aorta 320.

Figure 4:
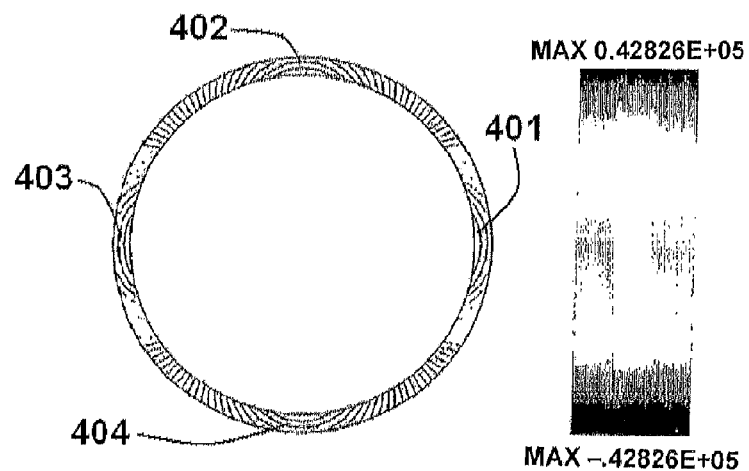
FIG. 4 shows $T_{11}$ changes with a maximum of $T_{11}$=42.826 KPa ($\theta$=0° and 180° in the inner circular) and minimum of $T_{11}$=−42.826 KPa ($\theta$=90° and 270° in the inner circular) according to an exemplary embodiment of the present invention.

An exemplary measurement of the stress tension exerted on the blood vessel and the changes in $T_{11}$ are shown in FIG. 4 according to an exemplary embodiment of the present invention. The maximum stress tension is exerted on the vessel at 401 and 403 while the minimum stress tension is exerted on the vessel at 402 and 404 when an exemplary embodiment of the present invention is used to stabilize the graft to the inside wall of the vessel by placing magnetic bodies on the external surface of the vessel. This calculation demonstrates that the stress levels are within biologically acceptable ranges. In other words, the stress distribution demonstrates that the computed Maxwell stresses are well within the physiological range of tissue stress and should not harm the tissue. Hence, the present invention does not overly perturb the vessel wall and should not induce an injury response or remodeling.

Figure 5:
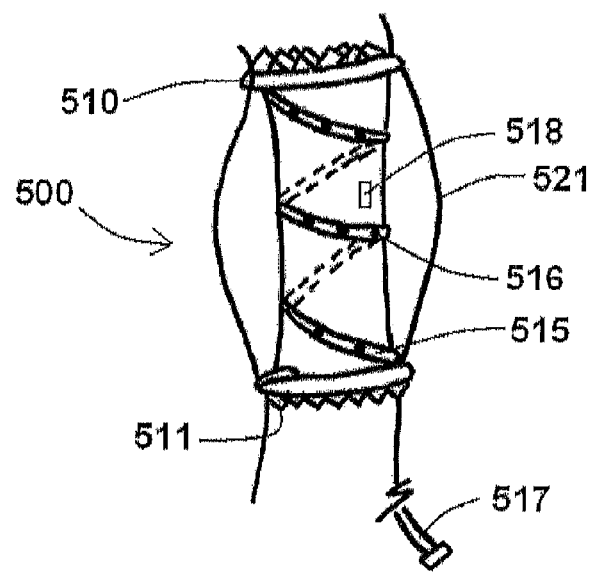
FIG. 5 shows a front view of a luminal stent graft within an aneurysm incorporating a perforated tube for controlling the fluid environment within the aneurysm and an optional pressure sensor as part of a telemetry system according to an exemplary embodiment of the present invention.

Yet another exemplary embodiment of the present invention is a graft assembly 600 as shown in FIG. 5. Assembly 500 includes magnetic bodies 510, magnetic polymer graft 511, tube 515 with tube openings 516, a catheter 517, and an optional pressure sensor 518. The tube 515 with tube openings 516 may function to suck or siphon out accumulated blood or other tissue or matter and to collapse the wall of the aneurysmic sack 521 to decrease blood-clot volume. This may reduce the stress in the aneurysmic sack 521 after deployment of magnet bodies 510 and decrease the risk of aneurysmic rupture. The catheter 517 may be connected to the tube 515 from the femoral artery such that a user is able to suction out accumulated blood or other matter. Alternatively, the tube openings 516 may function as an embolization device such that a biocompatible liquid polymer (e.g., ethylene venyl alcohol copolymer, cellulose, acetate polymer, cyanoacrylates or glue gel magnetic powder, or the like) may be introduced into the aneurysmic sack 521 via catheter 517 and through the tube openings 516 in order to pack the aneurysmic sack 521 and thereby reduce the possibility of endoleak or endotension. The tube 515 may be situated as depicted in FIG. 5 on the outer surface of the magnetic polymer graft 511 in a coiled fashion. The tube 515 may have tube openings 516 situated on the length of the tube 515 and may be spaced apart and of such a diameter so that the tube openings 516 may optimally function as described above. Additionally, the tube openings 516 may be a slit or any other geometric shape including but not limited to a pyramid in order to maximize the functioning of the tube openings 516 as previously described.

In order to ensure efficient deployment of the magnetic polymer graft 511 and magnetic bodies 510 (e.g., tight seal at the distal and proximal ends), it would be desirable to measure pressure in the aneurysmic sack 521. The optional pressure sensor 518 may be situated on the outer surface of the magnetic polymer graft 511 via mounting or gluing. The optional pressure sensor 518 may be in communication with an external telemetry monitoring system (not shown) via a wireless communication system (not shown). The optional pressure sensor 518 may be used to indicate whether or not a successful deployment of the magnetic polymer graft 511 has been achieved. In this case, the measured pressure will yield a pulsatile tracing initially before deployment of magnetic bodies 510 and magnetic polymer graft 511. Once the magnetic bodies 511 secure the proximal and distal ends of the aneurysmic sack 521, a tight seal between the magnetic bodies 510 and the surface of the aneurysmic sack 521 would eliminate the pulsatile tracing. This would provide indication of successful deployment. This can equally apply to the current art of stent grafts without magnets.

The optional pressure sensor 518 may also be used to monitor the patient's aneurysm by measuring the pressure within the aneurysmic sack 521. It may monitor the interior pressure of the aneurysmic sack 521 by measuring the local pressure outside of the wall of the magnetic polymer graft 511 and inside the outstretched wall of the ancurysmic sack 521. This would be of tremendous clinical value as the physician can monitor the status of the aneurysmic sack 521 and adapt treatment according to aneurysmic behavior. Currently, expensive and complicated imaging methods (such as MRI and CT) are used to monitor the dimension of the aneurysm longitudinally at discreet times (annually, etc.). Pressure is more relevant mechanically as a predictor of rupture and with telemetry it can be monitored continuously.

Although the above examples of the use of the present invention have been made in reference to an aneurysm, particularly an abdominal aortic aneurysm, the present invention is not limited to its use in correcting aneurysms. Many other uses are possible and within the purview of one having ordinary skill in the art. For example, the combination of a metallic material and a corresponding magnetic device may be used for the correction of the structure or architecture of organs, such as the heart or along other parts of the aorta or other vessels.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present inventions the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A device for controlling growth of an aneurysm, the device comprising
   a metallic body configured to be positioned within a lumen of an aneurysm, wherein an end-to-end length of the metallic body extends at least along a longitudinal length of the aneurysm;
   a tube with openings located on an outer surface of the metallic body, the tube configured to affect a fluid environment in an area between the outer surface of the metallic body and an inner wall surface of the aneurysm when the device is positioned within the lumen of the aneurysm; and
   at least one magnet configured to be positioned external to a vessel having the aneurysm, the at least one magnet, wherein when positioned external to the vessel, is further configured to magnetically hold the metallic body in position within the lumen of the aneurysm.

2. The device of claim 1, wherein the metallic body is an intravascular stent.

3. The device of claim 1, further comprising:
   a pressure sensor on the outer surface of the metallic body, the pressure sensor configured to monitor a pressure of an area between the outer surface of the metallic body and the inner wall surface of the aneurysm when the device is positioned within the lumen of the aneurysm.

4. The device of claim 3, wherein the pressure from the pressure sensor is monitored using a remote telemetry system operably coupled to the pressure sensor.

5. The device of claim 1, wherein the tube is capable of removing blood or other solutes from the aneurysm through the openings of the tube when the device is positioned within the lumen of the aneurysm.

6. The device of claim 1, wherein the tube is capable of introducing fluids, solutes, solutions or drugs into the aneurysm through the openings in the tube when the device is positioned within the lumen of the aneurysm.

7. The device of claim 1, wherein the at least one magnet comprises two magnets.

8. The device of claim 7, wherein each of the two magnets are completely or substantially circular in shape, the shape corresponding to an external circumferential shape of the vessel.

9. The device of claim 7, wherein when the two magnets are positioned external to the vessel, one of the two magnets is positioned external to the vessel at or near a first end of the metallic body, and the other of the two magnets is positioned external to the vessel at or near a second end of the metallic body.

10. The device of claim 1, wherein the metallic body comprises at least one metallic portion and at least one non-metallic portion.

11. The device of claim 1, further comprising:
    a magnet cover surrounding at least a portion of the metallic body; and
    bonded metallic powder positioned between the magnet cover and the metallic body.

12. The device of claim 1, further comprising:
    one or more magnetic beads or particles along the metallic body.

13. A device for controlling the growth of an aneurysm, the device comprising:
    an intravascular stent configured to be positioned within a lumen of an aneurysm, wherein an end-to-end length of the intravascular stent extends at least along a longitudinal length of the aneurysm;
    a tube with openings located on an outer surface of the intravascular stent, wherein the tube with openings is configured to remove blood or other solutes from an area between the outer surface of the intravascular stent and an inner wall surface of the aneurysm through the openings of the tube, and to introduce fluids, solutes, solutions or drugs into an area between the outer surface of the intravascular stent and an inner wall surface of the aneurysm; and
    at least one magnet configured to be positioned external to a vessel having the aneurysm, the at least one magnet, wherein when positioned external to the vessel, is further configured to magnetically hold the intravascular stent in position within the lumen of the aneurysm.

14. A method for providing magnetic tissue support, the method comprising:
    introducing a metallic body into an inside of a tissue that needs support, the metallic body comprising a tube with openings located on an outer surface of the metallic body, the tube configured to affect a fluid environment in an area between the outer surface of the metallic body and an inner wall surface of the tissue when the device is positioned within a lumen of the tissue; and
    introducing a magnet on the outside of the tissue that needs support so that the magnet and the metallic body form an attractive force across the tissue that needs support thereby providing support to the tissue.

15. The method of claim 14, wherein the step of introducing a magnet is performed by delivering the magnet using a procedure selected from the group consisting of an abdominal laparascopic procedure, a thoracoscopic procedure, a minimal surgical procedure, and an open surgical procedure.

16. The method of claim 14, wherein the introducing steps are performed using a percutaneous catheter.

17. The method of claim 14, wherein the tissue includes an aneurysm.

18. The method of claim 17, further comprising the step of:
    removing blood or other solutes from the aneurysm through openings of the tube when the metallic body is positioned within a lumen of the aneurysm.

19. The method of claim 17, further comprising the step of:
    introducing fluids, solutes, solutions or drugs into the aneurysm through openings in the tube when the metallic body is positioned within a lumen of the aneurysm.

20. The method of claim 17, wherein the metallic body comprises a pressure sensor on the outer surface of the metallic body, the pressure sensor configured to monitor a pressure of an area between the outer surface of the metallic body and the inner wall surface of the aneurysm when the metallic body is positioned within a lumen of the aneurysm, the method further comprising the step of:
    monitoring a pressure sensed by the pressure sensor using a remote telemetry system operably coupled to the pressure sensor.

21. The method of claim 14, wherein the step of introducing a metallic body comprises introducing a metallic body having an end-to-end length that extends at least along a longitudinal length of the tissue.

22. The method of claim 14, wherein the step of introducing a magnet comprises introducing a magnet to magnetically hold the metallic body in position within the inside of the tissue.

* * * * *